(12) United States Patent
Luo et al.

(10) Patent No.: US 12,178,929 B2
(45) Date of Patent: Dec. 31, 2024

(54) DISPLAY MODULE AND ELECTRONIC DEVICE

(71) Applicant: HKC Corporation Limited, Guangdong (CN)

(72) Inventors: Fei Luo, Guangdong (CN); Rongrong Li, Guangdong (CN)

(73) Assignee: HKC CORPORATION LIMITED, Guangdong (CN)

( * ) Notice: Subject to any disclaimer, the term of this patent is extended or adjusted under 35 U.S.C. 154(b) by 0 days.

(21) Appl. No.: 18/385,443

(22) Filed: Oct. 31, 2023

(65) Prior Publication Data

US 2024/0316232 A1 Sep. 26, 2024

(30) Foreign Application Priority Data

Mar. 23, 2023 (CN) .......................... 202310287259.8

(51) Int. Cl.
*A61L 2/10* (2006.01)
*A61L 2/24* (2006.01)
*A61L 2/26* (2006.01)

(52) U.S. Cl.
CPC .................................... *A61L 2/10* (2013.01); *A61L 2/24* (2013.01); *A61L 2/26* (2013.01); *A61L 2202/11* (2013.01);
(Continued)

(58) Field of Classification Search
CPC ..... A61L 2/10; A61L 2/24; A61L 2/26; A61L 2202/11; A61L 2202/14; A61L 2202/20
See application file for complete search history.

(56) References Cited

U.S. PATENT DOCUMENTS

| 11,360,630 B1 | 6/2022 | Li et al. |
| 2008/0142435 A1 | 6/2008 | Kawai et al. |

(Continued)

FOREIGN PATENT DOCUMENTS

| CN | 112578939 A | 3/2021 |
| CN | 113589586 A | 11/2021 |

(Continued)

OTHER PUBLICATIONS

Chinese First Office Action dated Apr. 25, 2023 issued in CN 202310287259.8.

(Continued)

*Primary Examiner* — Sean M Luck
(74) *Attorney, Agent, or Firm* — Scully, Scott, Murphy & Presser, P.C.

(57) ABSTRACT

Provided are a display module and an electronic device. The display module includes a display panel and a backlight module stacked with the display panel. The backlight module includes a light-emitting member, a light-guide member, and a back plate. The light-emitting member is configured to emit visible light. The light-guide member is disposed adjacent to the light-emitting member and configured to guide the visible light to the display panel. The back plate is configured to accommodate the light-emitting member and the light-guide member and defines a through-hole. The display module further includes a disinfection assembly. The disinfection assembly is at least partially accommodated in the through-hole or disposed at one side of the back plate away from the display panel, the disinfection assembly is configured to emit UV rays, the UV rays irradiate the display panel via the through-hole, and the disinfection assembly is detachably connected to the back plate.

16 Claims, 6 Drawing Sheets

(52) U.S. Cl.
CPC ....... *A61L 2202/14* (2013.01); *A61L 2202/20* (2013.01)

(56) References Cited

U.S. PATENT DOCUMENTS

| | | | |
|---|---|---|---|
| 2013/0045132 A1 | 2/2013 | Tumanov | |
| 2015/0258229 A1* | 9/2015 | Ha | A61L 2/208 422/291 |
| 2016/0093412 A1* | 3/2016 | Liao | A61L 2/10 250/221 |
| 2022/0088243 A1 | 3/2022 | Takahata | |
| 2022/0134128 A1 | 5/2022 | Kuzelka | |

FOREIGN PATENT DOCUMENTS

| | | | |
|---|---|---|---|
| CN | 113721791 A | 11/2021 |
| CN | 214633055 U | 11/2021 |
| JP | 2006204824 A | 8/2006 |
| WO | 2021163843 A1 | 8/2021 |
| WO | 2021178764 A1 | 9/2021 |

OTHER PUBLICATIONS

Decision to grant dated May 10, 2023 issued in CN 202310287259.8.

\* cited by examiner

FIG. 16

DISPLAY MODULE AND ELECTRONIC DEVICE

CROSS-REFERENCE TO RELATED APPLICATION

This application claims priority under 35 U.S.C. § 119(a) to Chinese Patent Application No. 202310287259.8, filed Mar. 23, 2023, the entire disclosure of which is incorporated herein by reference.

TECHNICAL FIELD

The present disclosure relates to the field of display device technologies, and in particular, to a display module and an electronic device.

BACKGROUND

With the development of artificial intelligence technologies, touch screens are becoming more and more popular in various fields such as office, scientific research, medical, in-vehicle, and aerospace.

However, since the touch screen is prone to breeding a large amount of viruses, bacteria, and the like due to touch of a user, especially public touch screens are used by many users, and are more likely to breed viruses and bacteria, which may have negative effect on users with weakened immune systems.

SUMMARY

In a first aspect, a display module is provided in the present disclosure. The display module includes a display panel and a backlight module stacked with the display panel. The backlight module includes a light-emitting member, a light-guide member, and a back plate. The light-emitting member is configured to emit visible light. The light-guide member is disposed adjacent to the light-emitting member and configured to guide the visible light emitted by the light-emitting member to the display panel. The back plate is configured to accommodate the light-emitting member and the light-guide member and defines multiple through-holes. The display module further includes a disinfection assembly. The disinfection assembly is at least partially accommodated in the through-holes or disposed at one side of the back plate away from the display panel. The disinfection assembly includes multiple disinfection members, each of the plurality of disinfection members is correspondingly accommodated in one of the multiple through-holes, and different disinfection members are accommodated in different through-holes, the multiple disinfection members are disposed corresponding to the light-guide member. the disinfection assembly is configured to emit ultraviolet (UV) rays, the UV rays irradiate the display panel via the through-holes and the light-guide member, and the disinfection assembly is detachably connected to the back plate. The light-guide member includes a first light-guide portion and multiple second light-guide portions. The first light-guide portion has a first light-incident surface and a light-exiting surface. The first light-incident surface is disposed corresponding to the light-emitting member. The visible light emitted by the light-emitting member is received via the first light-incident surface. The light-exiting surface is connected to the first light-incident surface in a bending manner, the light-exiting surface faces the display panel, and the visible light received via the first light-incident surface is emitted via the light-exiting surface to the display panel. The multiple second light-guide portions each is connected to the first light-guide portion in a bending manner. Each of the multiple second light-guide portions is correspondingly accommodated in one of the through-holes, and different second light-guide portions are accommodated in different through-holes. The second light-guide portions each have a second light-incident surface away from the first light-guide portion, the UV rays emitted by the disinfection members are received via the second light-incident surface, the second light-guide portions each are configured to guide the UV rays received to the first light-guide portion, and the UV rays guided by the second light-guide portions are emitted to the display panel via the light-exiting surface.

In a second aspect, an electronic device is provided in the present disclosure, and the electronic device includes a processor and the display module in the first aspect. The processor is electrically connected to the disinfection assembly in the display module and is configured to control the disinfection assembly; the processor is further electrically connected to the light-emitting member and the display panel in the display module; and the processor is configured to control the light-emitting member to emit visible light to the display panel so as to display a prompt, when the disinfection assembly operates.

BRIEF DESCRIPTION OF THE DRAWINGS

To explain technical solutions in implementations of the present disclosure more clearly, the following will give a brief introduction to accompanying drawings which are needed to be used in description of implementations. Apparently, the accompanying drawings described herein are merely some implementations of the present disclosure, and those of ordinary skills in the art may still derive other drawings from these accompanying drawings without creative efforts.

DETAILED DESCRIPTION

Technical solutions of implementations of the present disclosure will be described clearly and completely with reference to accompanying drawings in implementations of the present disclosure. Apparently, implementations described herein are merely some implementations, rather than all implementations, of the present disclosure. Based on implementations of the present disclosure, all other implementations obtained by those of ordinary skill in the art without creative effort shall fall within the protection scope of the present disclosure.

Terms "first", "second", and the like used in the specification, the claims, and the accompany drawings of the present disclosure are used to distinguish different objects rather than describe a particular order. In addition, the terms "include", "comprise", and "have" as well as variations thereof are intended to cover non-exclusive inclusion. For example, a process, a method, a system, a product, or a device including a series of operations or units is not limited to the listed operations or units, it can optionally include other operations or units that are not listed; alternatively, other operations or units inherent to the process, the method, the product, or the device can be included either.

A term "implementation" referred to herein means that a particular feature, structure, or characteristic described in conjunction with implementations may be contained in at least one implementation of the present disclosure. The phrase appearing in various places in the specification does not necessarily refer to the same implementation, nor does it refer an independent or alternative implementation that is mutually exclusive with other implementations. It is expressly and implicitly understood by those skilled in the art that an implementation described herein may be combined with other implementations.

Figure 1:
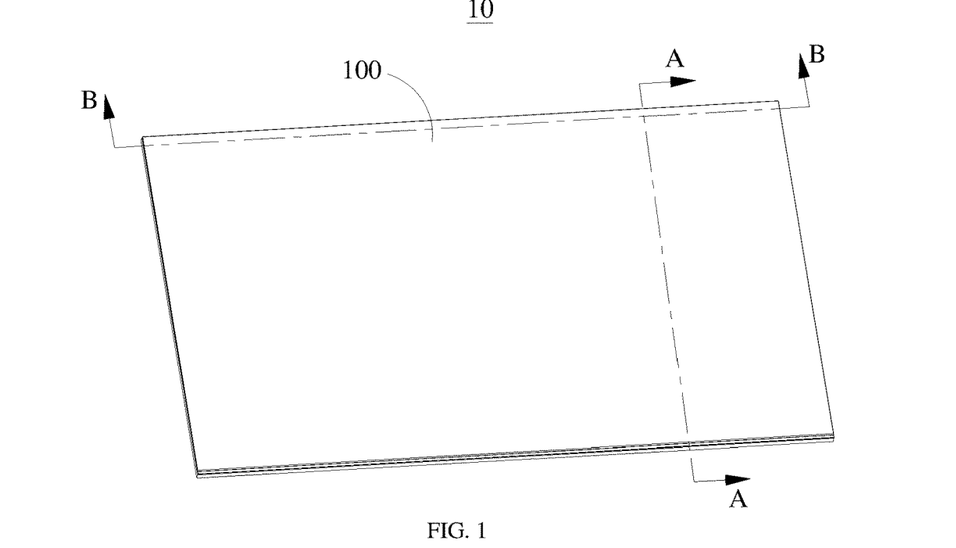
FIG. 1 is a schematic structural view of a display module provided in an implementation of the present disclosure.
Figure 2:
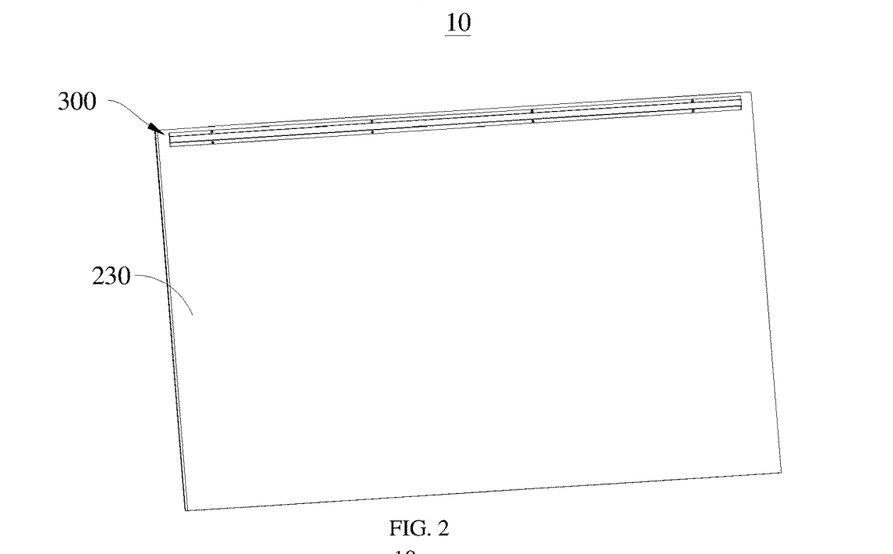
FIG. 2 is a schematic structural view of the display module in FIG. 1 from another viewing angle.
Figure 3:
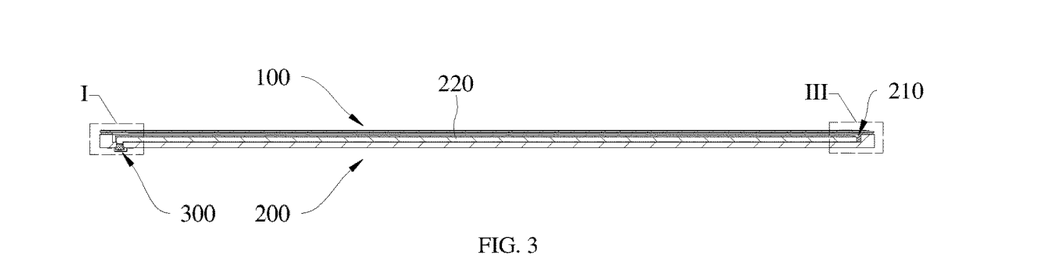
FIG. 3 is a schematic cross-sectional view taken along line A-A in FIG. 1.
Figure 4:
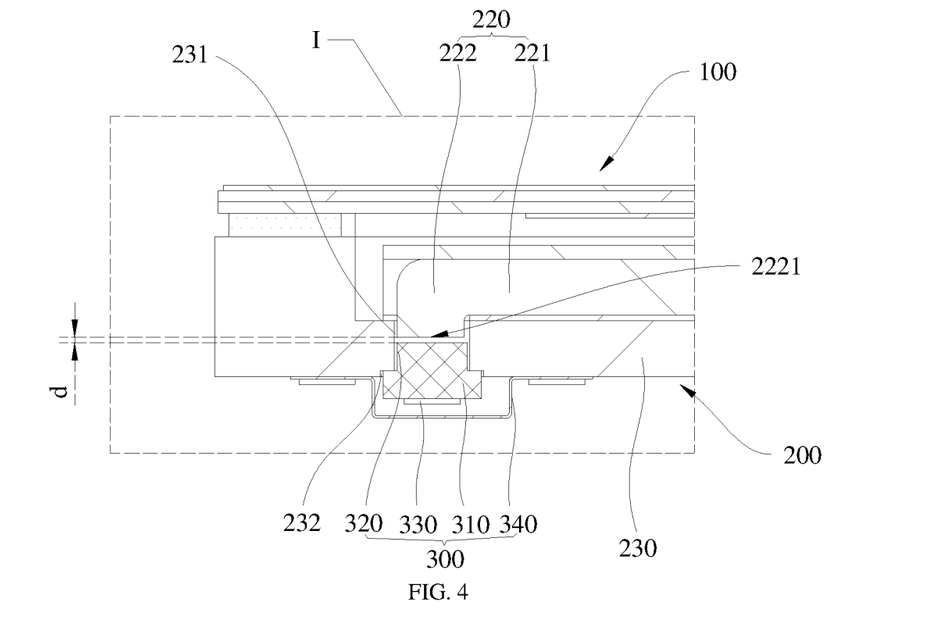
FIG. 4 is a partial enlarged schematic view at I in FIG. 3.
Figure 5:
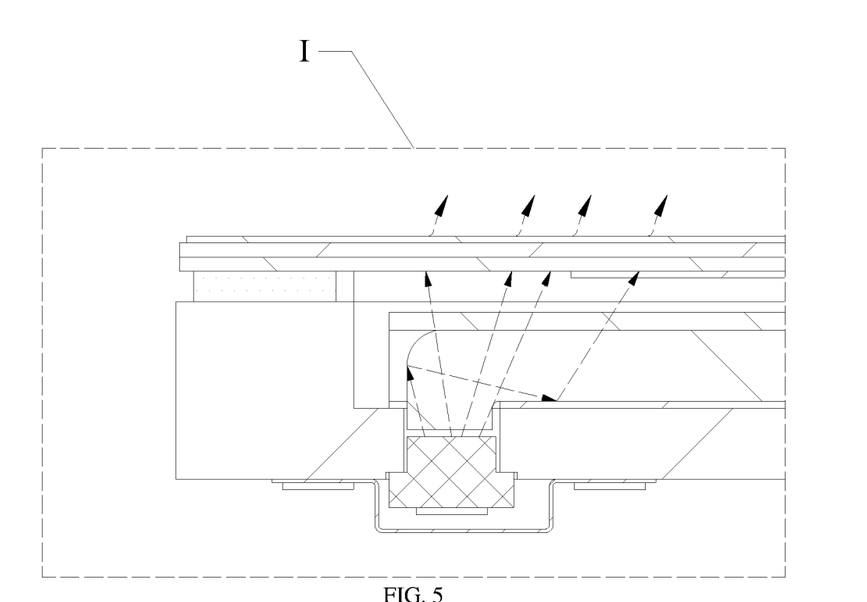
FIG. 5 is a schematic diagram illustrating a light path of ultraviolet (UV) rays emitted by a disinfection assembly in FIG. 4.
Figure 6:
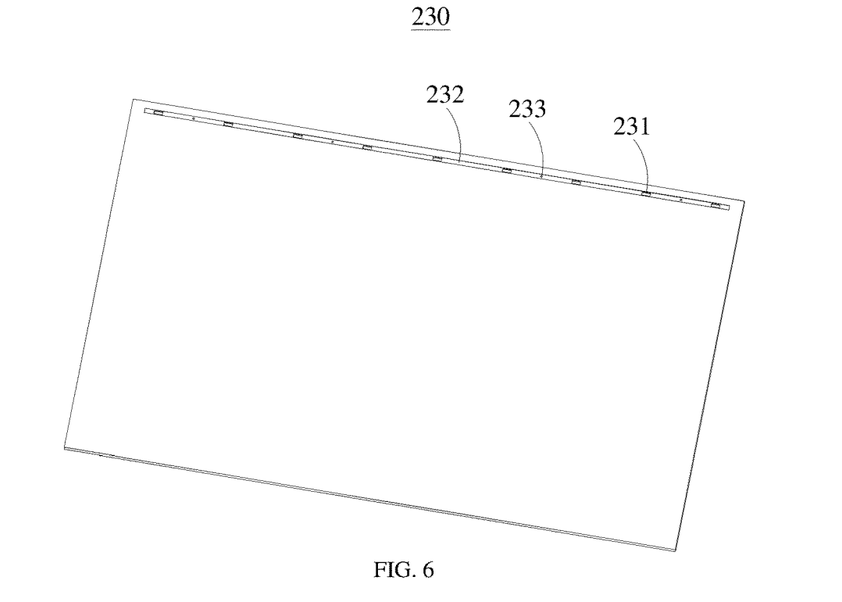
FIG. 6 is a schematic structural view of the back plate in FIG. 1.

A display module 10 is provided in the present disclosure. Please refer to FIGS. 1-6, where FIG. 1 is a schematic structural view of a display module provided an implementation of the present disclosure, FIG. 2 is a schematic structural view of the display module in FIG. 1 from another view, FIG. 3 is a schematic cross-sectional view taken along line A-A in FIG. 1, FIG. 4 is a partial enlarged schematic view at I in FIG. 3, FIG. 5 is a schematic diagram of a light path of ultraviolet (UV) rays emitted by a disinfection assembly in FIG. 4, FIG. 6 is a schematic structural view of the back plate in FIG. 1. In FIG. 3, in order to facilitate observation, a cross-sectional view is rotated by 90° C. clockwise for displaying. In this implementation, the display module 10 includes a display panel 100 and a backlight module 200 stacked with the display panel 100. The backlight module 200 includes a light-emitting member 210, a light-guide member 220, and a back plate 230. The light-emitting member 210 is configured to emit visible light. The light-guide member 220 is disposed adjacent to the light-emitting member 210 and is configured to guide the visible light emitted by the light-emitting member 210 to the display panel 100. The back plate 230 is configured to accommodate the light-emitting member 210 and the light-guide member 220, and the back plate 230 defines a through-hole 231. The display module 10 further includes a disinfection assembly 300, and the disinfection assembly 300 is at least partially accommodated in the through-hole 231 or disposed on one side of the back plate 230 away from the display panel 100. The disinfection assembly 300 is configured to emit UV rays, the UV rays irradiate the display panel 100 via the through-hole 231, and the disinfection assembly 300 is detachably connected to the back plate 230.

In this implementation, the display module 10 is applied to a display device, and is specifically applied to a display device with a touch screen, such as a ticket dispenser for train and subways, a machine control panel, a medical payment registration machine, a vehicle-mounted central control display screen, a mobile phone, a tablet computer, or the like.

In this implementation, in the display module 10, UV rays are emitted by the disinfection assembly 300 and irradiate the display panel 100 via the through-hole 231 of the back plate 230, so as to disinfect an outer surface of the display panel 100, thereby eliminating viruses, bacteria and the like on the outer surface of the display panel 100, achieving an self-cleaning effect of the display module 10, and further ensuring the health of the user. The UV rays emitted by the disinfection assembly 300 are electromagnetic waves with a wavelength in 270 nm-285 nm, which are invisible light and has excellent effects of disinfection and sterilization. The principle of sterilization and disinfection is that electromagnetic waves in this waveband can destroy a molecular structure of deoxyribonucleic acid (DNA) or ribonucleic acid (RNA) in microbial organism cells, resulting in growth cell death and/or regenerative cell death, achieving the effects of sterilization and disinfection. The disinfection assembly 300 is also referred to as a UV-ray light-emitting diode (LED) light bar.

Specifically, the back plate 230 defines a through-hole 231, and the disinfection assembly 300 is at least partially accommodated in the through-hole 231 or disposed on one side of the back plate 230 away from the display panel 100. The disinfection assembly 300 is detachably connected to the back plate 230, that is, the disinfection assembly 300 is detachably connected to an outer surface of the back plate 230, and the disinfection assembly 300 is disposed corresponding to the through-hole 231. The disinfection assembly 300 is detachably connected to the back plate 230, which facilitates replacement and maintenance of the disinfection assembly 300. In addition, the disinfection assembly 300 is at least partially accommodated in the through-hole 231 or disposed on one side of the back plate 230 away from the display panel 100, so that the disinfection assembly 300 may be exposed on one side of the back plate 230 away from the display panel 100, so that the disinfection assembly 300 can be directly disassembled outside the display module 10 without disassembling other components of the display module 10, which further facilitates replacement and maintenance of the disinfection assembly 300 and avoids damage to internal structures of the display module 10 (e. g., a foam adhesive, the display panel 100, the light-emitting member 210, the light-guide member 220, etc.). In addition, the display module 10 in this implementation achieves the effects of self-disinfection and self-sterilization by using the principle of UV disinfection, which breaks through a conventional concept of manual spraying or manual wiping for disinfection, and can not only efficiently disinfect the display panel 100, but also has advantages of low cost, significant savings in manpower and resources, and high feasibility. In addition, the UV rays emitted by the disinfection assembly 300 can also pass through the display panel 100 to disinfect the air around the display panel 100, thereby further ensuring the health of the user.

In addition, because the disinfection assembly 300 is at least partially accommodated in the through-hole 231 or disposed on one side of the back plate 230 away from the display panel 100, and is not directly disposed opposite to the light-emitting member 210 in a circumferential direction of the back plate 230, which prevents the disinfection assembly 300 from occupying an circumferential space of the back plate 230 additionally, thereby avoiding increasing a frame width of the back plate 230. Further, when two light-emitting members 210 are disposed on two opposite sides of the light-guide member 220, the disinfection assembly 300 is at least partially accommodated in the through-hole 231 or disposed on one side of the back plate 230 away from the display panel 100, and does not occupy installation space of the light-emitting members 210, thereby avoiding affecting installation of the light-emitting members 210. In this case, the light-guide member 220 can be adaptively configured to have two light-incident surfaces for visible light and one light-incident surface for UV rays.

Optionally, the disinfection assembly 300 may be detachably connected to the back plate 230 by means of, but not limited to, screw connection, snap-fitting, or hook and loop fastener bonding.

In conclusion, the display module 10 is provided in the present disclosure. The display module 10 includes the display panel 100, the backlight module 200, and the disinfection assembly 300. The backlight module 200 includes the back plate 230, the back plate 230 defines the through-hole 231, and the disinfection assembly 300 is at least partially accommodated in the through-hole 231 or on one side of the back plate 230 away from the display panel 100, so that the disinfection assembly 300 can emit UV rays, and the UV rays irradiate the display panel 100 via the through-hole 231, thereby disinfecting the display panel 100. In addition, the disinfection assembly 300 is detachably connected to the back plate 230, which facilitates replacement and maintenance of the disinfection assembly 300, and avoids damage to the internal structures of the display module 10. In addition, the principle of UV disinfection is used to achieve the effects of self-disinfection and self-sterilization, and a conventional concept of manual spraying or manual wiping for disinfection is broken through, which can not only efficiently disinfect the display panel 100, but also has advantages of low cost, significant savings in manpower and resources, and high feasibility. In addition, the UV rays emitted by the disinfection assembly 300 can also pass through the display panel 100 to disinfect the air around the display panel 100, thereby further ensuring the health of the user. Therefore, the display module 10 provided in the present disclosure can disinfect the display panel 100 with the disinfection assembly 300, and the disinfection assembly 300 is convenient for replacement and maintenance.

Figure 7:
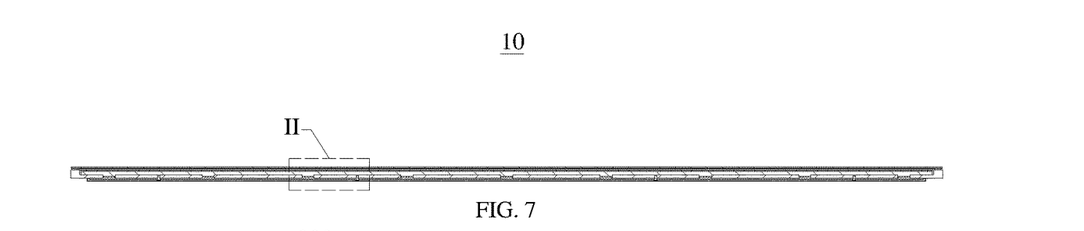
FIG. 7 is a schematic cross-sectional view taken along line B-B of FIG. 1.
Figure 8:
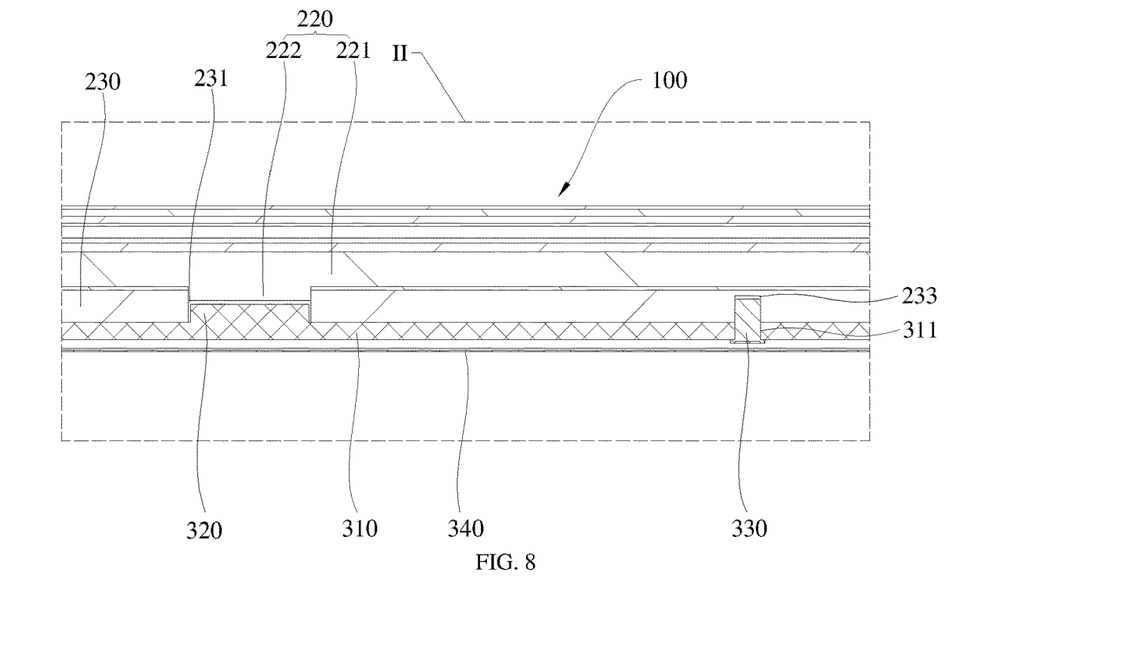
FIG. 8 is a partial enlarged schematic view at II in FIG. 7.

Please refer to FIG. 4, FIG. 7, and FIG. 8, where FIG. 7 is a schematic cross-sectional view taken along line B-B in FIG. 1, and FIG. 8 is a partially enlarged schematic view at II in FIG. 7. In this implementation, the back plate 230 defines a groove 232 and multiple through-holes 231, and the groove 232 is defined on one side of the back plate 230 away from the display panel 100. The multiple through-holes 231 are defined in a bottom wall of the groove 232 and are communicated with an accommodation space of the back plate 230 for accommodating the light-emitting member 210 and the light-guide member 220. The disinfection assembly 300 includes a carrier 310 and multiple disinfection members 320. The carrier 310 is at least partially accommodated in the groove 232. The multiple disinfection members 320 are carried on the carrier 310 and face towards the display panel 100, each of the multiple disinfection members 320 is correspondingly accommodated in one of the multiple through-holes 231, and different disinfection members 320 is accommodated in different through-holes 231.

In this implementation, the groove 232 is defined on one side of the back plate 230 away from the display panel 100, that is, the back plate 230 defines the groove 232 at a surface of the back plate 230 away from the display panel 100. The groove 232 is configured to accommodate at least part of the carrier 310. In one aspect, the groove 232 is configured to accommodate at least part of the carrier 310 to make the disinfection assembly 300 installed, thereby facilitating the installation of the carrier 310. On the other hand, a side wall of the groove 232 defined in the back plate 230 limits the carrier 310, so that the disinfection assembly 300 can be more stably installed on the back plate 230.

In this implementation, the multiple through-holes 231 are disposed corresponding to the multiple disinfection members 320. Each of the multiple through-holes 231 correspondingly accommodates one of the multiple disinfection members 320, different through-holes 231 are defined corresponding to different disinfection members 320, so as to form a limiting installation for the disinfection members 320, which facilitates alignment when the disinfection assembly 300 is installed on the back plate 230. In addition, the inner walls of the through-holes 231 defined in the back plate 230 can protect the disinfection members 320. The disinfection member 320 is also referred to as an UV LED lamp bead, and is configured to emit UV rays to the display panel 100 via the through-holes 231, so as to disinfect the display panel 100.

Referring to FIG. 3, FIG. 4, FIG. 7, and FIG. 8 again, in this implementation, the carrier 310 includes a first mating portion 311, and the first mating portion 311 is misaligned with the disinfection member 320. The back plate 230 includes a second mating portion 233 disposed corresponding to the first mating portion 311. The disinfection assembly 300 further includes a connector 330, and the connector 330 is detachably connected to the first mating portion 311 and the second mating portion 233.

In this implementation, that the first mating portion 311 is in fit with the second mating portion 233, which means that, in a stacking direction of the disinfection assembly 300 and the back plate 230, the first mating portion 311 and the second mating portion 233 are disposed opposite to each other. When the first mating portion 311 is in fit with the second mating portion 233, the connector 330 is configured to connect the first mating portion 311 and the second mating portion 233, so that the disinfection assembly 300 is installed on the back plate 230. The connector 330 can be detachably connected to the first mating portion 311 and the second mating portion 233, so that the disinfection assembly 300 can be disassembled from the back plate 230 at one side of the back plate 230 away from the display panel 100, thereby facilitating the disassembly and assembly of the disinfection assembly 300. In addition, the disinfection assembly 300 is assembled and disassembled without disassembling other components of the display module 10 (for example, the foam adhesive frame, the display panel 100, the light-emitting member 210, and the light-guide member 220), the assembling-and-disassembling loss of other components can be reduced, thereby reducing the assembling-and-disassembling costs of the disinfection assembly 300.

Optionally, the connector 330 may be, but not limited to, a screw, a pin, or the like.

Further, the first mating portion 311 is disposed to avoid the disinfection member 320, and the second mating portion 233 is disposed to avoid the through-hole 231, so that the connector 330 avoids the disinfection member 320, thereby preventing the assembling and normal operation of the disinfection member 320 from being affected.

Referring to FIG. 3, FIG. 4, FIG. 7, and FIG. 8 again, in this implementation, the disinfection assembly 300 further includes a shield 340. The shield 340 is disposed at one side of the carrier 310 away from the display panel 100. The shield 340 is detachably connected to the back plate 230, and the shield 340 covers the carrier 310.

In this implementation, the shield 340 covers one side of the carrier 310 away from the display panel 100, so as to cover the multiple disinfection members 320, thereby preventing UV rays emitted by the multiple disinfection members 320 from being emitted from one side of the back plate 230 away from the display panel 100, so as to avoid damage to the health of the user located at one side of the back plate 230 away from the display panel 100. In addition, because the shield 340 covers the carrier 310, the shield 340 protects the carrier 310 and the multiple disinfection members 320, thereby preventing the carrier 310 and the multiple disinfection members 320 from being damaged by external factors (such as oxidation and impact) of the display module 10. Because the shield 340 is disposed at the side of the carrier 310 away from the display panel 100, the shield 340 may be referred to as a rear cover.

Further, the shield 340 is detachably connected to the back plate 230, so as to facilitate disassembly and assembly of the carrier 310 and the multiple disinfection members 320, and facilitate replacement of the shield 340.

Optionally, the shield 340 may be detachably connected to the back plate 230 by, but not limited to, screws, buckles, or hook-and-loop fasteners.

Referring to FIG. 3, FIG. 4, and FIG. 5 again, in this implementation, the disinfection member 320 is disposed corresponding to the light-guide member 220, and UV rays emitted by the disinfection member 320 are emitted to the display panel 100 via the light-guide member 220.

In this implementation, since the disinfection member 320 is disposed corresponding to the light-guide member 220, the UV rays emitted by the disinfection member 320 can be scattered by the light-guide member 220 to be emitted out uniformly, so that the coverage of the UV rays is wider and the UV rays cover the display panel 100 uniformly, thereby improving the disinfection effect of the disinfection member 320.

Figure 9:
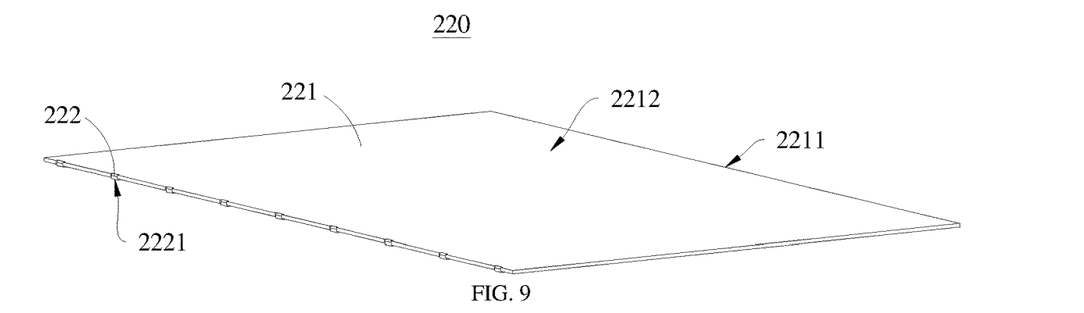
FIG. 9 is a schematic structural view of a light-guide member in FIG. 1.
Figure 10:
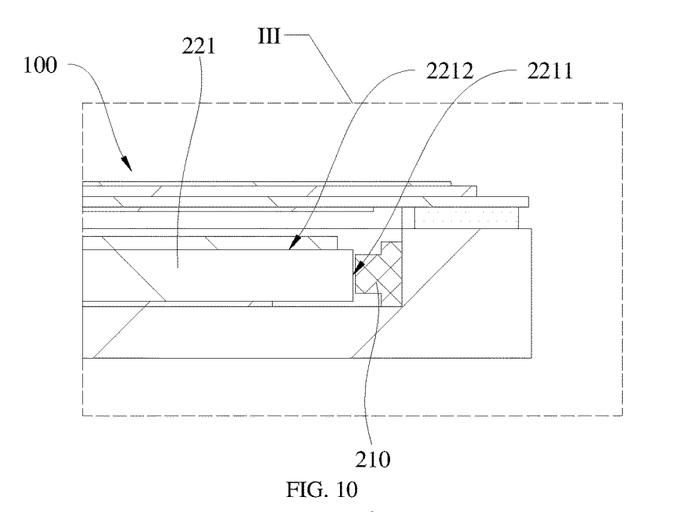
FIG. 10 is a partial enlarged schematic view at III in FIG. 3.

Further, please refer to FIGS. 3 to 5, FIG. 9, and FIG. 10 together, where FIG. 9 is a schematic structural view of the light-guide member in FIG. 1, and FIG. 10 is a partial enlarged schematic view at III in FIG. 3. In this implementation, the light-guide member 220 includes a first light-guide portion 221 and multiple second light-guide portions 222. The first light-guide portion 221 has a first light-incident surface 2211 and a light-exiting surface $_{2212}$. The first light-incident surface 2211 is disposed corresponding to the light-emitting member 210 and the visible light emitted by the light-emitting member 210 is received via the first light-incident surface 2211. The light-exiting surface 2212 is connected to the first light-incident surface 2211 in a bending manner, and the light-exiting surface 2212 faces the display panel 100. Visible light received via the first light-incident surface 2211 is emitted via the light-exiting surface 2212 to the display panel 100. The multiple second light-guide portions 222 are connected to the first light-guide portion in a bending manner, each of the second light-guide portions 222 is correspondingly accommodated in one of the through-holes 231, and different second light-guide portions 222 are accommodated in different through-holes 231. The multiple second light-guide portion 222 each have a second light-incident surface 2221 away from the first light-guide portion 221, and the UV rays emitted by the disinfection members 320 are received via the second light-incident surface 2221. The multiple second light-guide portions 222 each are configured to guide the UV rays received to the first light-guide portion 221, and the UV rays guided by the second light-guide portions 222 are emitted to the display panel 100 via the light-exiting surface 2212.

In this implementation, the multiple second light-guide portions 222 are connected to the first light-guide portion 221 in a bending manner, such that each second light-guide portion 222 is correspondingly accommodated in one of the through-holes 231, and each second light-guide portion 222 is disposed corresponding to one disinfection member 320, so that each of the second light-guide portions 222 can receive, via the second light-incident surface 2221, the UV rays emitted by the disinfection member 320, thereby improving the absorption of the UV rays by the light-guide member 220 is improved, and the disinfection effect of the disinfection member 320 on the display panel 100.

Optionally, the second light-guide portion 222 has a reflective surface connected to the second light-incident surface 2221 in a bending manner, and the light-exiting surface is disposed closer to a side wall of the back plate 230 than the first light-guide portion 221. The light-guide member 220 further includes a reflective film or reflective particles, and the reflective film or reflective particles are carried on the reflective surface and are configured to reflect the UV rays incident via the second light-incident surface 2221 to the first light-guide portion 221, so that the first light-guide portion 221 can receive the UV rays better.

Optionally, a visible-light transmission structure is disposed at the first light-incident surface 2211, so as to prevent UV rays from transmitting through the first light-incident surface 2211 to the light-emitting member 210 to influence visible-light emission of the light-emitting member 210. An UV-ray transmission structure is disposed at the second light-incident surface 2221, so as to prevent visible light from transmitting through the second light-incident surface 2221 to the disinfection assembly 300 to influence UV-ray emission of the disinfection assembly 300. The visible-light transmission structure is a transparent film structure, a mesh dot distribution structure, or a particle distribution structure, that allows visible light to transmit but does not allow UV rays to transmit. The UV-ray transmission structure is a transparent film structure, a mesh dot distribution structure, or a particle distribution structure, that allows UV rays to transmit but does not allow visible light to transmit.

Optionally, the light-emitting member 210 may be, but not limited to, a light-emitting diode (LED), a mini LED, or a micro LED.

Figure 11:
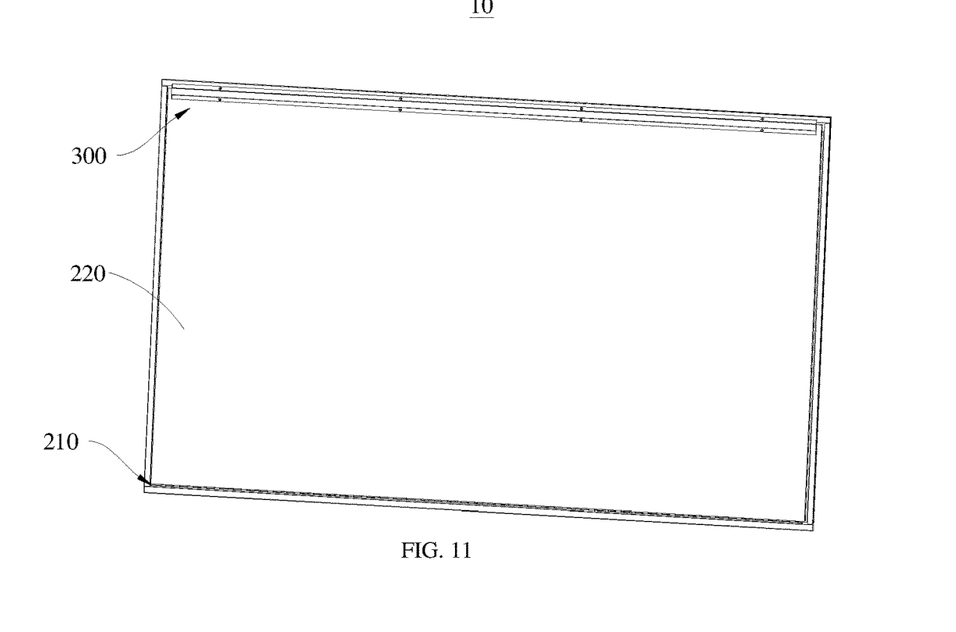
FIG. 11 is a schematic view illustrating positions of a disinfection assembly and a light-emitting member relative to a light guide.

Please further refer to FIG. 3 to FIG. 5 and FIG. 9 to FIG. 11, where FIG. 11 is a schematic view illustrating positions of a disinfection assembly and a light-emitting member relative to a light-guide member. In this implementation, in a direction perpendicular to the light-exiting surface 2212, the first light-incident surface 2211 and the second light-incident surface 2221 are located at different sides of the first light-guide portion 221.

In other words, in this implementation, in a direction perpendicular to the light-exiting surface 2212, the disinfection assembly 300 and the light-emitting member 210 are located at different sides of the first light-guide member 221, so as to prevent the disinfection assembly 300 from occupying a mounting position of the light-emitting member 210, thereby avoiding poor product function of the display module 10. For example, a dark shadow of the display panel 100 in a region close to the light-emitting member 210 can be avoided.

Optionally, the first light-guide portion 221 has two long sides opposite to each other and two short sides opposite to each other, and the long side and the short side are connected in a bending manner. The disinfection assembly 300 is disposed adjacent to one of the two long sides, and the light-emitting member 210 is disposed adjacent to the other one of the two long sides, so that a distance for transmitting the UV rays emitted by the disinfection assembly 300 is reduced, and a distance for transmitting the visible light emitted by the light-emitting member 210 is reduced, thereby facilitating the UV rays and the visible light to cover the display panel 100. One side of the display module 10 where the disinfection assembly 300 is located may be referred to as a top side, and one side of the display module 10 where the light-emitting member 210 is located may be referred to as a bottom side.

Referring to FIG. 4 again, in this implementation, the second light-guide portion 222 is spaced apart from the disinfection member 320, and a distance d between the second light-guide portion 222 and the disinfection member 320 satisfies 0<d≤0.3 mm.

In this implementation, the second light-guide portion 222 is spaced apart from the disinfection member 320, and a mounting margin space is reserved for the disinfection member 320 to be mounted on the back plate 230, thereby preventing the second light-guide portion 222 from abutting against the second light-guide portion 222 due to factors such as a size tolerance and a temperature change of the disinfection member 320 and the carrier 310, and further preventing damage to the disinfection member 320. Specifically, the distance d between the second light-guide portion 222 and the disinfection member 320 satisfies: 0<d≤0.3 mm, which can not only prevent the disinfection member 320 from abutting against the second light-guide portion 222, but also prevent affecting absorption of UV rays emitted by the disinfection member 320 by the second light-guide portion 222. When d>0.3 mm, the gap between the second light-guide member 222 and the disinfection assembly 320 is so large, that the UV rays emitted by the disinfection member 320 are too dispersed before entering the second light-guide member 222, and a part of the UV rays are emitted to an inner wall of the back plate 230 which defines the through-hole 231 to generate loss, which is not beneficial to the entry of the UV rays into the second light-guide member 222. Therefore, the distance d between the second light-guide portion 222 and the disinfection member 320 satisfies: 0<d≤0.3 mm, which can not only prevent the disinfection member 320 from abutting against the second light-guide portion 222, but also prevent affecting absorption of the UV rays emitted by the disinfection member 320 by the second light-guide portion 222. For example, the distance d between the second light-guide portion 222 and the disinfection member 320 may be, but is not limited to, 0.1 mm, or 0.2 mm, or 0.3 mm, or any other arbitrary value which is greater than 0 and less than or equal to 0.3 mm.

In addition, referring to FIG. 4 again, the display module 10 further includes an adhesive frame for bonding the display panel 100 and the back plate 230. The adhesive frame is a foam adhesive frame, so that the adhesive frame provides an elastic buffer while bonding the display panel 100 and the back plate 230, and plays a buffering role when the display module 10 is subjected to external impacts.

Optionally, the backlight module 200 further includes a light-reflective layer which is disposed on a surface of the first light-guide portion 221 away from the display panel 100, so as to assist the first light-guide portion 221 in reflecting the UV rays emitted by the disinfection member 320 to the display panel 100, thereby improving the disinfection effect of the disinfection member 320 on the display panel 100.

Optionally, the backlight module 200 further includes an optical film disposed between the first light-guide portion 221 and the display panel 100. The optical film is configured to scatter and equalize the UV rays emitted from the light-exiting surface 2212 of the first light-guide portion 221, so as improve the coverage and uniformity of the UV rays projected onto the display panel 100, thereby improving the disinfection effect on the display panel 100.

Further, the optical film is attached to the light-exiting surface 2212, so as to further improve the scattering and light-equalizing effect of the optical film on the UV rays emitted from the light-exiting surface 2212.

In this implementation, the disinfection assembly 300 is fast and efficient in disinfecting the display panel 100, and specifically, the disinfection assembly 300 only needs 10 minutes to 20 minutes to complete disinfection of the display panel 100. For example, the disinfection assembly 300 only needs 10 min, 12 min, 15 min, 18 min, 20 min, or other value between 10 min and 20 min to complete the disinfection of the display panel 100.

Figure 12:
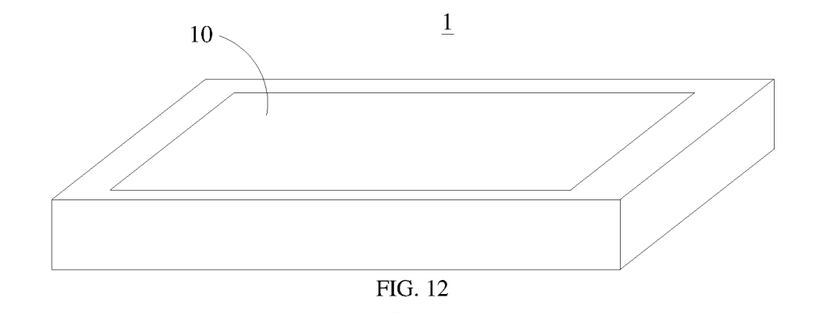
FIG. 12 is a schematic structural view of an electronic device provided an implementation of this application.
Figure 13:
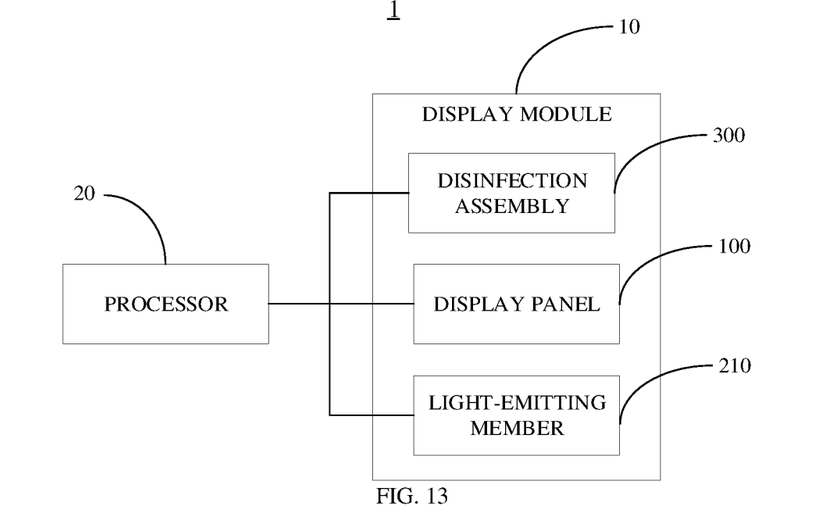
FIG. 13 is a block diagram illustrating electrical connections in the electronic device in FIG. 12.
Figure 14:
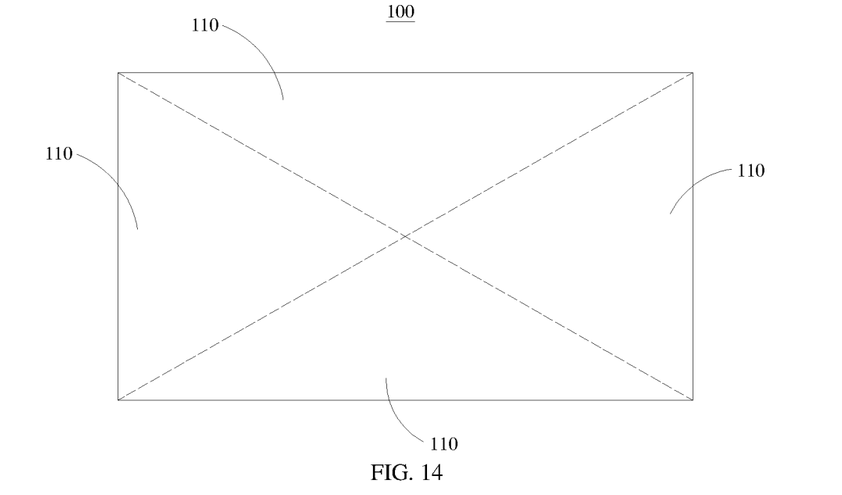
FIG. 14 is a schematic diagram illustrating a partition of a display panel provided in an implementation of the present disclosure.

An electronic device 1 is further provided in the present disclosure. Referring to FIG. 4, FIG. 12, and FIG. 13, where FIG. 12 is a schematic structural view of an electronic device provided in an implementation of the present disclosure, and FIG. 13 is a block diagram illustrating electrical connections in the electronic device in FIG. 12. In this implementation, the electronic device 1 includes a processor 20 and the display module 10 in any one of the foregoing implementations. The processor 20 is electrically connected to the disinfection assembly 300 in the display module 10 and controls the disinfection assembly 300. The processor 20 is further electrically connected to the light-emitting member 210 and the display panel 100 in the display module 10. When the disinfection assembly 300 operates, the processor 20 is configured to control the light-emitting member 210 to emit visible light to the display panel 100 so as to display a prompt.

In this implementation, the electronic device 1 is a display device having a touch screen. For example, the electronic device 1 may be, but is not limited to, a ticket dispenser for train and subways, a machine control panel, a medical payment registration machine, a vehicle-mounted central control display screen, a mobile phone, a tablet computer, or the like.

In this implementation, the processor 20 is configured to control on and off of the disinfection assembly 300. When the processor 20 controls the disinfection assembly 300 to work, the processor 20 is further configured to control the light-emitting member 210 and the display panel 100 to operate, to make the light-emitting member 210 emit visible light to the display panel 100, so as to display a prompt on the display panel 100, and the prompt is used to prompt the user to be far away from the electronic device 1, thereby preventing UV rays emitted by the disinfection assembly 300 from damaging the health of a user. For example, the prompt may be "in UV disinfection, do not approach", or "dangerous, do not approach", so long as the prompt can serve as a warning.

Therefore, the electronic device 1 provided in the present disclosure can not only control the disinfection assembly 300 in the display module 10 to emit UV rays so as to disinfect the display panel 100 of the display module 10, but also warn the user to keep away when the disinfection assembly 300 is operating, so as to avoid damage to the health of the user.

Further, when the disinfection assembly 300 operates, the processor 20 is further configured to control the prompt to move on the display panel 100, so as to prevent afterimage from being formed on the display panel 100.

Optionally, the processor 20 may, but is not limited to, control the prompt to vertically roll, horizontally roll, or obliquely roll on the display panel 100, as long as the prompt can move on the display panel 100.

Figure 15:
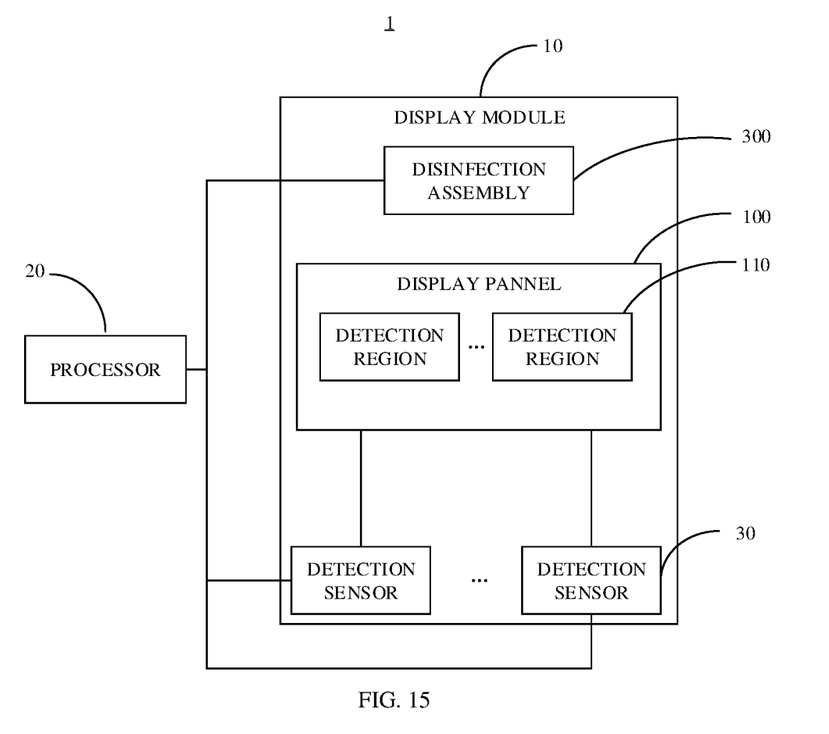
FIG. 15 is a block diagram illustrating an electrical connection between a processor and a detection sensor in FIG. 14.

Further, as illustrated in FIG. 15, the display module 10 further includes a detection sensor 30, and when the detection sensor 30 detects that the display panel 100 is touched while the disinfection assembly 300 is operating, the processor 20 controls the disinfection assembly 300 to stop working, so as to prevent the health of the user from being damaged by UV rays.

Optionally, in an implementation, the display module 10 further includes the detection sensor 30 electrically connected to the display panel 100 for detecting whether the display panel 100 is touched. The processor 20 is electrically connected to the detection sensor 30, and is configured to record the number of times that the display panel 100 is touched and obtain a first number of times of detection, and compare of the first number of times of detection and the first preset number of times. When the processor 20 determines that the first number of times of detection is greater than or equal to the first preset number of times, the processor 20 controls the disinfection assembly 300 to emit UV rays.

In this implementation, the detecting sensor detects whether or not the display panel 100 is touched, and records and obtains the first number of times of detection by the processor 20. An accumulated level of bacteria, viruses and the like on the surface of the display panel 100 after being touched by the user can be deduced from the first number of times of detection. When the processor 20 determines that the first number of times of detection is greater than or equal to the first preset number of times, which means bacteria, viruses and the like accumulated on the surface of the display panel 100 reach a degree that cleaning and disinfection are required, the processor 20 controls the disinfection assembly 300 to emit UV rays to disinfect the display panel 100, such that the display panel 100 is cleaned to prevent bacteria, viruses and the like on the display panel 100 from damaging the health of the user. The first preset number of times may be set according to an actual application condition, which is not limited herein.

Optionally, the detection sensor 30 may be, but not limited to, a pressure sensor, and the pressure sensor detects whether the display panel 100 is touched by detecting a pressure generated when a user touches the display panel 100. Alternatively, the detection sensor 30 may be an optical sensor, and the optical sensor detects whether the display panel 100 is touched by detecting a distance between a user's finger and the display panel 100. Alternatively, the detection sensor 30 may be a temperature sensor, and the temperature sensor detects whether the display panel 100 is touched by detecting a temperature change on the display panel 100.

Optionally, in an implementation, as illustrated in FIG. 11, the display module 10 includes multiple disinfection assemblies 300. The display panel 100 includes multiple detection regions 110. The multiple disinfection assemblies 300 each is disposed corresponding to one of the detection regions 110. The display module 10 includes multiple detecting sensors. The multiple detection sensors 30 are electrically connected to the display panel 100, each of the detection sensors 30 is configured to detect whether one of the detection regions 110 is touched, different detection sensors 30 are configured to detect whether one of the detection regions 110 is touched, and different detection sensors 30 are configured to detect different regions. The processor 20 is electrically connected to the multiple detection sensors 30 and is configured to record the number of times each of the detection regions 110 is touched and obtain multiple second numbers of times of detection. The processor 20 is configured to determine a detection region 110, the second number of times of detection of which is greater than or equal to the second preset number of times, as a region to-be-disinfected. When the processor 20 determines at least one of the multiple detection regions 110 as the region to-be-disinfected, the processor 20 is configured to control the disinfection assembly 300 disposed corresponding to the region to-be-disinfected to emit UV rays.

In this implementation, the detection region 110 is a virtually divided region, so that the detection sensor 30 performs corresponding detection and the disinfection assembly 300 performs corresponding disinfection. It can be understood that the detection region 110 is not physically divided, that is, the display panel 100 is an integrated structure.

In this implementation, the detecting sensor detects whether or not a detection region 110 on the display panel 100 is touched, and records and obtains the second number of times of detection by the processor 20. The accumulated level of bacteria, viruses and the like on the surface of the display panel 100 after the detection region 110 is touched by the user can be deduced from the second number of times of detection. When the processor 20 determines that the second number of times of detection is greater than or equal to the second preset number of times, which means that, bacteria, viruses and the like accumulated on the surface of the display panel 100 in the detection region 110 reach a degree that cleaning and disinfection are required, the processor 20 determines the detection region 110 as a region to-be-disinfected, and the processor 20 controls the disinfection assembly 300 corresponding to the region to-be-disinfected to UV rays so as to disinfect the display panel 100 in the detection region 110. In this way, the display panel 100 is cleaned to prevent bacteria, viruses and the like on the display panel 100 from damaging the health of the user. The second preset number of times may be set according to an actual application condition, which is not limited herein.

In this implementation, the display panel 100 is divided into multiple detection regions 110, so as to perform detection respectively and clean and disinfect independently, thereby realizing accurate detection and disinfection on each detection region 110 of the display panel 100, and avoiding unnecessary disinfection on a region which does not need disinfection, thereby improving disinfection efficiency and reducing disinfection costs.

In this implementation, multiple detection regions 110 are connected, and two adjacent detection regions 110 do not have an overlapping region, thereby facilitating the detection of the detection regions 110 by the sensor. It should be understood that each of the detection regions 110 may be correspondingly close to one disinfection assembly 300, and different detection regions 110 may be correspondingly close to different disinfection assemblies 300.

In other implementations, there is an overlapping region between different detection regions 110, wherein each of the detection regions 110 is correspondingly a region on the display panel 100 covered by the UV rays emitted by the disinfection assembly 300. Since it is difficult for the UV rays emitted by the multiple disinfection assembly 300 to have no overlapping region on the display panel 100. Therefore, there is an overlapping region between different detection regions 110, which helps to disinfect the display panel 100 by using the disinfection assembly 300 to the maximum extent.

Optionally, in an implementation, the display module 10 further includes the detection sensor 30 electrically connected to the display panel 100 for detecting whether the display panel 100 is touched. The processor 20 is electrically connected to the detection sensor 30 and is configured to record the number of times that the display panel 100 is touched and obtain a third number of times of detection. The processor 20 is configured to count the third number of times of detection in each time period in a historical preset number of days to obtain a first time period and a second time period. The first time period is a time period in which the third number of times of detection is less than or equal to a preset threshold. The second time period is a time period in which the third number of times of detection is greater than the preset threshold. When the processor 20 determines that the current moment is in the first time period and the display panel 100 is not touched currently, the processor 20 controls the disinfection assembly 300 to be turned on. When the processor 20 determines that the current moment is in the second time period, the processor 20 controls the disinfection assembly 300 to be turned off or kept in a turned-off state. The preset threshold may be set according to an actual application, which is not limited herein.

In this implementation, the processor 20 is configured to count the third number of times of detection in each time period in a historical preset number of days to obtain the first time period and the second time period. The first time period is a time period in which the user uses the electronic device 1 (namely, the user touches the display panel 100) less frequently, the second time period is a time period in which the user uses the electronic device 1 more frequently. The first time period and the second time period together form one day. It may be appreciated that a day may include multiple first time periods and multiple second time periods.

In this implementation, by making statistics of the first time period and the second time period, the processor 20 can control the disinfection assembly 300 to achieve full-automatic intelligent cleaning and disinfection, thereby improving the disinfection efficiency for the display panel 100 and effectively avoiding the user.

Alternatively, the historical preset number of days may be, but is not limited to, one week, one month, one quarterly, or the like.

Further, the processor 20 regularly updates the first time period and the second time period, so as to deal with different situations in which the electronic device 1 is used in different periods, and further optimize the disinfection of the display panel 100 by the disinfection assembly 300.

Optionally, the periodic updating can be carried out by the processor 20 at intervals which may be, but is not limited to, one month, one quarter, one year, or the like.

Figure 16:
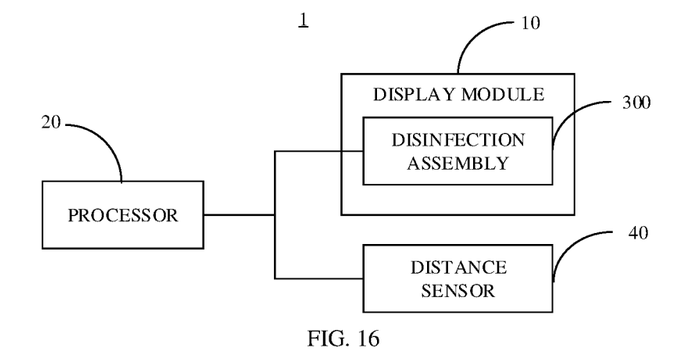
FIG. 16 is a block diagram illustrating an electrical connection between a processor and a distance sensor in FIG. 12.

Alternatively, in an implementation, as illustrated in FIG. 16, the electronic device 1 further includes a distance sensor 40, and the distance sensor 40 is configured to detect a current distance between a living body outside the display module 10 and the display module 10. The processor 20 is electrically connected to the distance sensor 40, and is configured to receive the current distance and compare the current distance with the preset distance. When the disinfection assembly 300 is emitting UV rays to disinfect the display panel 100 and the processor 20 determines that the current distance is less than or equal to the predetermined distance, the processor 20 is configured to control the disinfection assembly 300 to stop emitting UV rays.

In this implementation, when the disinfection assembly 300 is emitting UV rays to disinfect the display panel 100, the distance sensor 40 detects the current distance between the living body outside the display module 10 and the display module 10, where the living body refers to the user.

When the disinfection assembly 300 is emitting UV rays to disinfect the display panel 100, and the processor 20 determines that the current distance is less than or equal to the preset distance, the processor 20 is configured to control the disinfection assembly 300 to stop emitting UV rays, so as to prevent the UV rays from irradiating the user to damage the health of the user. When the processor 20 determines that the current distance is greater than the predetermined distance, the processor 20 controls the disinfection assembly 300 to restart, so as to continue to disinfect the display panel 100. The preset distance is set according to an actual situation, which is not limited herein. For example, greater power of the disinfection assembly 300 will lead to greater preset distance.

Further, a first preset distance and a second preset distance are set, where the first preset distance is greater than the second preset distance. When the processor 20 determines that the current distance is less than or equal to the first preset distance, the processor 20 determines whether the living body has a moving tendency towards the display module 10, that is, calculates a change rate at which the current distance is close to the second preset distance, so as to calculate a moving acceleration of the living body towards the display module 10, and compares the moving acceleration with a preset moving acceleration. When the processor 20 determines that the moving acceleration is greater than or equal to the preset moving acceleration, or when the processor 20 determines that the current distance is less than or equal to the second preset distance, the processor 20 controls the disinfection assembly 300 to stop emitting UV rays. The first preset distance is set, to prevent a situation where the living body moves toward the display module 10 too fast for the processor 20 to control the disinfection assembly 300 to stop emission of UV rays in time.

Although the implementations of the present disclosure have been shown and described, it should be understood that the above implementations are illustrative and cannot be construed as limitations to the present disclosure. Those skilled in the art can make changes, modifications, replacements, and variations to the above implementations within the scope of the present disclosure, and these changes and modifications shall also belong to the scope of protection of the present disclosure.

What is claimed is:

1. A display module, comprising a display panel and a backlight module stacked with the display panel, wherein the backlight module comprises:
- a light-emitting member configured to emit visible light;
- a light-guide member disposed adjacent to the light-emitting member and configured to guide the visible light emitted by the light-emitting member to the display panel; and
- a back plate configured to accommodate the light-emitting member and the light-guide member and defining a plurality of through-holes;

wherein the display module further comprises:
- a disinfection assembly, wherein the disinfection assembly is at least partially accommodated in the through-holes or disposed at one side of the back plate away from the display panel, wherein the disinfection assembly comprises a plurality of disinfection members, each of the plurality of disinfection members is correspondingly accommodated in one of the plurality of through-holes, and different disinfection members are accommodated in different through-holes, the plurality of disinfection members are disposed corresponding to the light-guide member, the disinfection assembly is configured to emit ultraviolet (UV) rays, the UV rays irradiate the display panel via the through-holes and the light-guide member, and the disinfection assembly is detachably connected to the back plate;

wherein the light-guide member comprises:
- a first light-guide portion, wherein the first light-guide portion has a first light-incident surface and a light-exiting surface, the first light-incident surface is disposed corresponding to the light-emitting member, the visible light emitted by the light-emitting member is received via the first light-incident surface, the light-exiting surface is connected to the first light-incident surface in a bending manner, the light-exiting surface faces the display panel, and the visible light received via the first light-incident surface is emitted via the light-exiting surface to the display panel; and
- a plurality of second light-guide portions, wherein the plurality of second light-guide portions each is connected to the first light-guide portion in a bending manner, and each of the plurality of second light-guide portions is correspondingly accommodated in one of the through-holes, different second light-guide portions are accommodated in different through-holes; and the second light-guide portions each have a second light-incident surface away from the first light-guide portion, the UV rays emitted by the disinfection members are received via the second light-incident surface, the second light-guide portions each are configured to guide the UV rays received to the first light-guide portion, and the UV rays guided by the second light-guide portions are emitted to the display panel via the light-exiting surface.

2. The display module of claim 1, wherein the back plate further defines a groove, the groove is defined on one side of the back plate away from the display panel, the plurality of through-holes are defined in a bottom wall of the groove and are communicated with an accommodation space of the back plate for accommodating the light-emitting member and the light-guide member;

wherein the disinfection assembly further comprises:
- a carrier at least partially accommodated in the groove, wherein the plurality of disinfection members are carried on the carrier and face towards the display panel.

3. The display module of claim 2, wherein the carrier comprises a first mating portion, and the first mating portion is misaligned with the plurality of disinfection members; the back plate comprises a second mating portion, and the second mating portion is disposed corresponding to the first mating portion; and the disinfection assembly further comprises a connector detachably connecting to the first mating part and the second mating part.

4. The display module of claim 3, wherein the first mating portion is disposed to avoid the plurality of disinfection members, and the second mating portion is disposed to avoid the plurality of through-holes.

5. The display module of claim 2, wherein the disinfection assembly further comprises:
- a shield disposed at one side of the carrier away from the display panel, the shield being detachably connected to the back plate, and the shield covering the carrier.

6. The display module of claim 1, wherein the first light-guide portion has two long sides opposite to each other and two short sides opposite to each other, the disinfection assembly is disposed adjacent to one of the two long sides, and the light-emitting member is disposed adjacent to the other one of the two long sides.

7. The display module of claim 1, wherein in a direction perpendicular to the light-exiting surface, the first light-incident surface and the second light-incident surface are located at different sides of the first light-guide portion.

8. The display module of claim 1, wherein in each of the through-holes, the second light-guide portion is spaced apart from the disinfection member, and a distance d between the second light-guide portion and the disinfection member satisfies: $0<d\leq0.3$ mm.

9. An electronic device comprising a processor and a display module, wherein the display module comprises a display panel and a backlight module stacked with the display panel, and the backlight module comprises:
- a light-emitting member configured to emit visible light;
- a light-guide member disposed adjacent to the light-emitting member and configured to guide the visible light emitted by the light-emitting member to the display panel; and
- a back plate configured to accommodate the light-emitting member and the light-guide member and defining a plurality of through-holes;

wherein the display module further comprises:
- a disinfection assembly, wherein the disinfection assembly is at least partially accommodated in the through-holes or disposed at one side of the back plate away from the display panel, wherein the disinfection assembly comprises a plurality of disinfection members, each of the plurality of disinfection members is correspondingly accommodated in one of the plurality of through-holes, and different disinfection members are accommodated in different through-holes, the plurality of disinfection members are disposed corresponding to the light-guide member, the disinfection assembly is configured to emit ultraviolet (UV) rays, the UV rays irradiate the display panel via the through-holes and the light-guide member, and the disinfection assembly is detachably connected to the back plate;

wherein the light-guide member comprises:
- a first light-guide portion, wherein the first light-guide portion has a first light-incident surface and a light-exiting surface, the first light-incident surface is disposed corresponding to the light-emitting member, the visible light emitted by the light-emitting member is received via the first light-incident surface, the light-exiting surface is connected to the first light-incident surface in a bending manner, the light-exiting surface faces the display panel, and the visible light received via the first light-incident surface is emitted via the light-exiting surface to the display panel; and a plurality of second light-guide portions, wherein the plurality of second light-guide portions each is connected to the first light-guide portion in a bending manner, and each of the plurality of second light-guide portions is correspondingly accommodated in one of the through-holes, different second light-guide portions are accommodated in different through-holes; and the second light-guide portions each have a second light-incident surface away from the first light-guide portion, the UV rays emitted by the disinfection members are received via the second light-incident surface, the second light-guide portions each are configured to guide the UV rays received to the first light-guide portion, and the UV rays guided by the second light-guide portions are emitted to the display panel via the light-exiting surface; wherein, the processor is electrically connected to the disinfection assembly and is configured to control the disinfection assembly; the processor is further electrically connected to the light-emitting member and the display panel; and the processor is configured to control the light-emitting member to emit visible light to the display panel so as to display a prompt when the disinfection assembly operates.

10. The electronic device of claim 9, wherein the back plate further defines a groove, the groove is defined on one side of the back plate away from the display panel, the plurality of through-holes are defined in a bottom wall of the groove and are communicated with an accommodation space of the back plate for accommodating the light-emitting member and the light-guide member;

wherein the disinfection assembly further comprises:
a carrier at least partially accommodated in the groove, wherein the plurality of disinfection members are carried on the carrier and face towards the display panel.

11. The electronic device of claim 10, wherein the carrier comprises a first mating portion, and the first mating portion is misaligned with the plurality of disinfection members; the back plate comprises a second mating portion, and the second mating portion is disposed corresponding to the first mating portion; and the disinfection assembly further comprises a connector detachably connecting to the first mating part and the second mating part.

12. The electronic device of claim 10, wherein the disinfection assembly further comprises:
a shield disposed at one side of the carrier away from the display panel, the shield being detachably connected to the back plate, and the shield covering the carrier.

13. The electronic device of claim 9, wherein the first light-guide portion has two long sides opposite to each other and two short sides opposite to each other, the disinfection assembly is disposed adjacent to one of the two long sides, and the light-emitting member is disposed adjacent to the other one of the two long sides.

14. The electronic device of claim 9, wherein in a direction perpendicular to the light-exiting surface, the first light-incident surface and the second light-incident surface are located at different sides of the first light-guide portion.

15. The electronic device of claim 9, wherein in each of the through-holes, the second light-guide portion is spaced apart from the disinfection member, and a distance d between the second light-guide portion and the disinfection member satisfies: $0<d\leq0.3$ mm.

16. The electronic device of claim 9, wherein the processor is further configured to control the prompt to move on the display panel when the disinfection assembly operates.

\* \* \* \* \*